United States Patent [19]

Adachi et al.

[11] Patent Number: 5,096,697

[45] Date of Patent: Mar. 17, 1992

[54] METHOD OF STIMULATING HAIR GROWTH WITH ALIPHATIC ALCOHOLS

[75] Inventors: Kuniaki Adachi; Hideo Tamai, both of Kanagawa; Masanao Sadai, Hiratsuka, all of Japan

[73] Assignee: Lion Corporation, Tokyo, Japan

[21] Appl. No.: 397,634

[22] Filed: Aug. 23, 1989

Related U.S. Application Data

[63] Continuation of Ser. No. 72,041, Jul. 1, 1987, abandoned, which is a continuation of Ser. No. 848,756, Apr. 7, 1986, abandoned, which is a continuation of Ser. No. 620,263, Jun. 13, 1984, abandoned.

[30] Foreign Application Priority Data

Jun. 21, 1983 [JP] Japan .................. 58-110184

[51] Int. Cl.$^5$ .......................... A61K 7/06; A61K 7/15; A61K 9/06; A61K 9/12

[52] U.S. Cl. ..................... 424/47; 252/106; 252/107; 424/59; 424/60; 424/63; 424/64; 424/65; 424/68; 424/69; 424/70; 424/73; 514/783; 514/828; 514/844; 514/845; 514/846; 514/847; 514/873; 514/880; 514/881; 514/887; 514/929; 514/944

[58] Field of Search .................. 514/728, 738; 424/70, 424/47

[56] References Cited

PUBLICATIONS

FDA Consumer, 2/1981, vol. 15, No. 1, pp. 10 to 12.

*Primary Examiner*—Dale R. Ore
*Attorney, Agent, or Firm*—Bacon & Thomas

[57] ABSTRACT

Cell-stimulating composition having hair-growing effect and skin-vivifying effect. The composition comprising as an effective ingredient an aliphatic alcohol having odd number of carbon atoms or a derivative thereof in a cosmetically acceptable carrier.

1 Claim, No Drawings

METHOD OF STIMULATING HAIR GROWTH WITH ALIPHATIC ALCOHOLS

This application is a continuation of application Ser. No. 07/072,041, filed July 1, 1987, now abandoned, which is a continuation of Ser. No. 06/848,756, filed Apr. 7, 1986, now abandoned, which is a continuation of Ser. No. 06/620,263, filed June 13, 1984, now abandoned.

BACKGROUND OF THE INVENTION

I. Field of the Invention

This invention relates to a cell-stimulating composition such as hair-growing composition and skin-stimulating cosmetic composition and a method of stimulating cells.

II. Description of the Prior Art

Cell-stimulating compositions-such as hair-growing compositions and skin-stimulating cosmetic compositions containing various pharmacological agents are known. Such pharmacological agents contained in conventional hair-growing compositions include a vitamin such as vitamin E, an amino acid such as serine or methionine, a vasodilator such as an acetylcholine derivative, an anti-inflammatory agent such as lithospermum root extract, a female sex hormone such as estradiol, skin function stimulant such as cepharanthine, a melanine synthesis catalyst such as copper pantothenate, a keratolytic such as salicylic acid. Pharmacological agent contained in conventional skin-stimulating compositions include vitamins such as vitamin E and vitamin C, amino acids or metabolites thereof such as pyrrolidonecarboxylic acid, pharmacological plant extracts such as aloe extract.

However, it seems that a satisfactory effect has not yet been obtained.

SUMMARY OF THE INVENTION

Therefore, the object of the present invention is to provide an effective cell-stimulating composition and a method of stimulating cells.

This invention provides a cell-stimulating composition comprising as an effective ingredient an effective amount of an aliphatic alcohol having an odd number of carbon atoms or a derivative thereof in a cosmetically acceptable carrier.

This invention also provides a method of stimulating cells comprising applying an effective amount of an aliphatic alcohol having an odd number of carbon atoms or a derivative thereof onto a skin.

According to the present invention, great cell-stimulating effect can be obtained.

DETAILED DESCRIPTION OF THE PREFERRED EMBODIMENTS

Alopecia may arise from various causes. In each case, individual hairs cannot complete their normal hair cycle to reach the telogen state. In order to decrease baldness and accelerate hair generation, it is necessary to bring the hair follicles from the telogen state into the normal anagen state. As a result of extensive research into the conversion of hair from the telogen state into the anagen state, it has been found that an aliphatic alcohol having an odd number of carbon atoms and a derivative thereof exhibit a remarkable hair-growing effect. Further study revealed that it has broader effect in cell-stimulation. This invention is based on this discovery.

Cell-stimulation effect includes hair-growing effect and skin-vivifying effect. Skin-vivifying effect includes the promotion of skin moisture and the increase of the blood flow in the skin, thereby preventing and/or healing chaps, chilblains and skin roughness.

The aliphatic alcohol to be used for the cell-stimulating composition of the present invention may be a saturated or unsaturated aliphatic alcohol provided it has an odd number of carbon atoms. The unsaturated aliphatic alcohol may contain a plurality of double bonds. The aliphatic alcohol may be a lower aliphatic alcohol such as propionyl alcohol (having 3 carbon atoms) or amyl alcohol (having 5 carbon atoms), or a higher aliphatic alcohol such as tricosyl alcohol (having 23 carbon atoms) or pentacosyl alcohol (having 25 carbon atoms). Further, the hydroxyl group can bind to any of the carbon atoms. Preferred aliphatic alcohol having an odd number of carbon atoms may include n-propionyl alcohol, n-amyl alcohol, n-heptyl alcohol, n-nonyl alcohol, n-undecyl alcohol, n-tridecyl alcohol, n-pentadecyl alcohl, n-heptadecyl alcohol, n-nonadecyl alcohol, n-uneicosyl alcohol, n-tricosyl alcohol, and n-pentacosyl alcohol.

For the cell-stimulating composition of the present invention, derivatives of an aliphatic alcohol having an odd number of carbon atoms hereinabove described may also be used as an effective ingredient. Representative of the derivatives are esters and ethers of the aliphatic alcohol.

Preferred esters include esters with organic acid, such as carboxylate (carboxylates of which carboxylic residue has 2 to 24 carbon atoms are especially preferred), succinate, citrate, fumarate, lactate, pyruvate, malate, and oxaloacetate, and esters with inorganic acid, such as phosphate.

Preferred ethers include ethers with aliphatic alcohols (aliphatic alcohols containing 2 to 24 carbon atoms are especially preferred); polyols such as glycerin, polyglycerin, ethyleneglycol, propyleneglycol, butane-diol; and sugars such as glucose, ribose, galactose, arabinose, mannose, xylose, sorbitol and mannitol. The ether can contain 2 or more alcohol residue of odd number of carbon atoms such as di- or tri-odd numbered alkoxide of glycerin.

It should be noted that the essential requirement for the derivatives to be used in the present invention is that they contain an aliphatic alcohol residue of odd numbered carbon atoms. Therefore, for example, the acid residue in the above-mentioned esters can be substituted with various substituent. Similarly, the alcohol residue or the sugar residue in the above ether can be substituted with various substituent. However, needless to say, the derivative cannot be harmful to human body.

The cell-stimulating effect of the composition of the present invention can be further promoted by incorporating therein an aliphatic carboxylic acid having an odd number of carbon atoms or a derivative thereof. The aliphatic carboxylic acid to be used may be a saturated or unsaturated aliphatic carboxylic acid. The unsaturated aliphatic carboxylic acid may contain a plurality of double bonds. The aliphatic carboxylic acid may be a lower aliphatic carboxylic acid such as propionic acid (having 3 carbon atoms) or valeric acid (having 5 carbon atoms), or a higher aliphatic carboxylic acid such as tricosanoic acid (having 23 carbon atoms) or pentacosanoic acid (having 25 carbon atoms). Preferred aliphatic carboxylic acids having an odd number of carbon atoms may include propionic acid, valeric acid, heptanoic acid, nonanoic acid, undecanoic acid, tridecanoic acid, pentadecanoic acid, heptadecanoic acid, nonadecanoic acid, heneicosanoic acid, tricosanoic acid and pentacosanoic acid.

Derivatives of the aliphatic carboxylic acid having an odd number of carbon atoms may also contribute to the promotion of the effectiveness of the composition. Preferred derivatives include esters, salts and amides of the aliphatic carboxylic acid having an odd number of carbon atoms. Examples of such derivatives include the following.

A) monoglycerides represented by the formula (I) or (II):

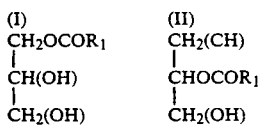

wherein $R_1$ is a straight-chain aliphatic group having an even number of carbon atoms.

B) diglycerides represented by the formula (III) or (IV):

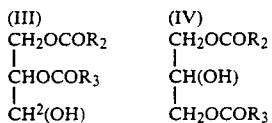

wherein at least one of $R_2$ and $R_3$ is a straight-chain aliphatic group having an even number of carbon atoms. It should be noted here that the promotion of the effect of the present invention can be achieved if one of $R_2$ and $R_3$ represents an aliphatic group having an even number of carbon atoms while the other represents hydrogen or an aliphatic group having an odd number of carbon atoms or another organic group which does not adversely affect the human body. However, a diglyceride of an aliphatic carboxylic acid having an odd number of carbon atoms is particularly preferred.

C) triglycerides represented by the formula (V):

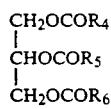 (V)

wherein at least one of $R_4$, $R_5$ and $R_6$ is a straight-chain aliphatic group having an even number of carbon atoms. It should be noted here that, where at least one of $R_4$, $R_5$ and $R_6$ is an aliphatic group having an even number of carbon atoms, the effect sought by the present invention can be enhanced even if the others are in each case hydrogen or an aliphatic group having an odd number of carbon atoms or another organic group which does not adversely affect the human body. However, a triglyceride of an aliphatic carboxylic acid having an odd number of carbon atoms is particularly preferred.

D) aliphatic carboxylic acid salts represented by the formula (VI):

 (VI)

wherein $R_7$ is a straight-chain aliphatic group having an even number of carbon atoms, M is a metal atom, and n is an integer corresponding the valence of M. Representatives may be $R_7COONa$, $R_7COOK$ and $R_7COOLi$.

E) esters represented by the formula (VII):

wherein $R_8$ is a straight-chain aliphatic group having an even number of carbon atoms, $R_9$ is a residue of a primary or secondary alcohol, an amine residue, a polyoxyethylene residue, a sorbitan residue or a sucrose residue. A representative primary alcohol may be methanol and ethanol, and a representative amine residue is mono-, di- and tri-ethanolamine.

F) primary amides represented by the general formula (VIII):

wherein R is a straight-chain aliphatic group having an even number of carbon atoms, and $R_{11}$ and $R_{12}$ are independently hydrogen or an organic group having no adverse effect on the human body.

G) secondary amides represented by the formula (IX):

wherein at least one of $R_{13}$ and $R_{14}$ is a straight-chain aliphatic group having an even number of carbon atoms, and $R_{15}$ may be a hydrogen atom or any organic group which does not adversely affect the human body. It should be noted here that where at least one of $R_{13}$ and $R_{14}$ is an aliphatic group having an even number of carbon atoms the effect of the present invention can be enhanced, and that the other may be any organic group which does not adversely affect the human body, although it is particularly preferred that both be a straight-chain aliphatic group having an even number of carbon atoms.

H) tertially amides represented by the formula (X):

wherein at least one of $R_{16}$, $R_{17}$, and $R_{18}$ is a straight-chain aliphatic group having an even number of carbon atoms. It is to be noted that where at least one of $R_{16}$, $R_{17}$ and $R_{18}$ is an organic group with an even number of carbon atoms, the effect of the present invention can be promoted, and also that the others may each be any organic group exerting no adverse influence on the human body. However, it is particularly preferred that all three be independently a straight-chain aliphatic group having an even number of carbon atoms.

I) dibasic carboxylic acids represented by the formula (XI) or salts thereof:

wherein $R_{19}$ is a straight-chain aliphatic group having an odd number of carbon atoms.

J) sterol esers represented by the formula (XII):

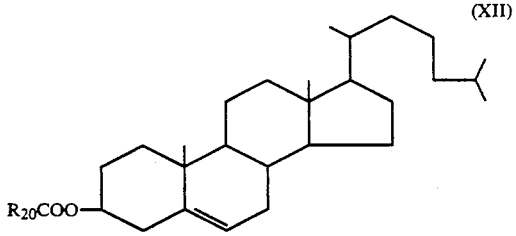

wherein $R_{20}$ is a straight-chain aliphatic group having an even number of carbon atoms.

K) phospholipids represented by the formula (XIII):

wherein at least one of $R_{21}$ and $R_{22}$ is a straight-chain aliphatic group having an even number of carbon atoms, and the other may be hydrogen or an organic group having no adverse effect on the human body. However, it is preferred that both of $R_{21}$ and $R_{22}$ are independently a straight-chain aliphatic group having an even number of carbon atoms. X is a choline residue, an ethanolamine residue, a serine residue or an inositol residue. When X is choline residue, it represents a phosphatidyl choline. When X is ethanolamine residue, it represents a phosphatidyl ethanolamine. When X is serine residue, it represents a phosphatidyl serine. When X is inositol residue, it represents a phosphatidyl inositol.

L) phsphatidic acids represented by the formula (XIV):

wherein at least one of $R_{23}$ and $R_{24}$ is a straight-chain aliphatic group having an even number of carbon atoms, and the other is hydrogen or an organic group having no adverse effect on the human body. However, it is preferred that both of $R_{23}$ and $R_{24}$ are independently a straight-chain aliphatic group having an even number of carbon atoms.

M) sphingolipids represented by the formula (XV):

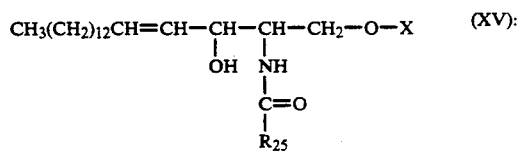

wherein $R_{25}$ is a straight-chain aliphatic group having an even number of carbon atoms, and X is a sugar residue, a phosphate residue or an amine residue such as choline or ehtanolamine.

In addition to the above-mentioned effective ingredients, the cell-stimulating composition of the present invention contains a cosmetically acceptable carrier. Such a carrier is not described in detail here since it is well known in this field. Examples of such a carrier include water; ethanol; a polyol such as ethylene glycol, propylene glycol, 1,3-butylene glycol, glycerin or sorbitol; a siloxane such as dimethyl polysiloxane, phenyl polysiloxane or polyoxyalkylene polysiloxane; an animal or vegetable oil such as sperm oil or jojoba oil; liquid paraffin; vaseline; paraffin wax; squalane; and an olefin oligomer.

The cell-stimulating composition of the present invention may contain an effective ingredient that is conventionally used. Such an effective ingredient may include, for example, a vitamin such as vitamin E, a hormone such as estradiol, a vasodilator such as an acetylcholine derivative, an amino acid such as serine or methionine, an anti-inflammatory agent such as lithospermum root extract, a skin function stimulant such as cepharanthine, or a keratolytic such as salicylic acid.

The cell-stimulating composition of the present invention may be used in a conventional manner and has a variety of applications. When used as a hair-growing agent, the applications include endermic liniment, hair tonic, hair lotion, hair cream, hair shampoo, hair rinse or the like. When used as a skin-vivifying agent, it can be used as, for example, pharmaceutical cream or lotion for treating asteatosis cutis, chaps, chilblains and skin roughness; external cosmetics such as skin cosmetics, lipcream, lipstick, sunny care agent, a detergent; and after-shaving cream or lotion. Specified in more detail, the cosmetics include creams such as emollient cream, cleansing cream, foundation cream, massage cream, vanishing cream, nutrient cream, hand cream, sun screen cream and shaving cream; lotions such as emollient lotion, cleansing lotion, foundation lotion, hand lotion, astringent lotion, after-shaving lotion, suntan lotion and after-sunburn lotion; soap; pack; powders such as face powder, compact powder, talcum powder, baby powder and deodorant powder; sticks such as lipstick and deodorant stick; rouge; sprays such as deodorant spray; and bath salt, bath oil and other skin cosmetics. Since the ingredients of the composition of the present invention are oil-soluble, it can be easily formulated as, for example, emulsion ointment, fatty ointment, alcohol-based lotion or the like. Further, the composition of the present invention may be in the form of, for example, water-based solution, alcohol-based solution, w/o emulsion, o/w emulsion, w/o/w multilayer emulsion, powder, stick, spray and paste.

The effective ingredients of the composition may preferably be contained in the amount of 0.01 to 30% by weight. The dose of application is not critical since the composition has no side effects.

Test 1: Animal Study for Evaluating Effectiveness

Aliphatic alcohols having an odd number of carbon atoms and derivatives thereof were tested for their hair-growing effects.

The tested substances were linear saturated aliphatic alcohols having carbon atoms in variously odd and even numbers, and esters thereof. Test samples were prepared by dissolving each test substance in ethanol. Concentration of the test substance were 0.3, 1.0, and 5.0% by weight, respectively. As a control, ethanol containing no test substance was also tested.

The test animals were groups of 6 to 8 male rabbits of New Zealand White species each weighing about 2.5 kg from whose backs hair was removed. Rabbits in the telogen state alone were used. The test sample was applied in the amount of 0.2 ml twice per week for 30 to 60 days to the area of the rabbits' backs from which the hair had been removed. The test was conducted by observing the number of days required for the conversion of hair from the telogen state into the anagen state. The results are shown in Table 1 below. In the Table, "shortened days" means the number of days by which the conversion of the telogen state into anagen state is shortened, compared with the control in which ethanol containing no test substance was applied. For example, when the number of shortened days is 10, it means that the coversion of telogen state in anagen state occurred 10 days earlier than the control experiment.

TABLE 1

| Test Substance | Concentration (% by weight) | Hair-Growing Effect Shortened Days | Overall Evaluation |
|---|---|---|---|
| Amyl Alcohol | 1.0 | 10 | Effective |
| Heptyl Alcohol | 1.0 | 12 | Effective |
| Nonyl Alcohol | 1.0 | 18 | Effective |
| Undecyl Alcohol | 1.0 | 26 | Remarkably Effective |
| Tridecyl Alcohol | 1.0 | 26 | Remarkably Effective |
| Pentadecyl Alcohol | 1.0 | 26 | Remarkably Effective |
| Heptadecyl Alcohol | 1.0 | 22 | Effective |
| Nonadecyl Alcohol | 1.0 | 20 | Effective |
| Uneicosyl Alcohol | 1.0 | 16 | Effective |
| Trieicosyl Alcohol | 1.0 | 12 | Effective |
| Pentaeicosyl Alcohol | 1.0 | 12 | Effective |
| Butyl Alcohol | 1.0 | 0 | Ineffective |
| Hexyl Alcohol | 1.0 | 2 | Ineffective |
| Octyl Alcohol | 1.0 | 0 | Ineffective |
| Decyl Alcohol | 1.0 | 4 | Ineffective |
| Lauryl Alcohol | 1.0 | 2 | Ineffective |
| Myristyl Alcohol | 1.0 | 0 | Ineffective |
| Cetyl Alcohol | 1.0 | 0 | Ineffective |
| Stearyl Alcohol | 1.0 | 2 | Ineffective |
| Eicosyl Alcohol | 1.0 | 0 | Ineffective |
| Behenyl Alcohol | 1.0 | 0 | Ineffective |
| Lignoceryl Alcohol | 1.0 | 0 | Ineffective |
| Nonyl Succinate | 0.3 | 16 | Effective |
| Decyl Succinate | 0.3 | 5 | Ineffective |
| Undecanyl Succinate | 0.3 | 24 | Effective |
| Nonyl Citrate | 0.3 | 16 | Effective |
| Decyl Citrate | 0.3 | 2 | Ineffective |
| Undecanyl Citrate | 0.3 | 20 | Effective |
| Nonyl Fumarate | 0.3 | 14 | Effective |
| Decyl Fumarate | 0.3 | 0 | Ineffective |
| Undecanyl Fumarate | 0.3 | 22 | Effective |
| Undecyl Decanoate | 5.0 | 26 | Remarkably Effective |
| Undecyl Linoleate | 5.0 | 28 | Remarkably Effective |
| Lauryl Decanoate | 5.0 | 0 | Ineffective |
| Lauryl Linoleate | 5.0 | 3 | Ineffective |
| Tridecyl Decanoate | 5.0 | 22 | Effective |
| Tridecyl Linoleate | 5.0 | 26 | Remarkably Effective |

It can be seen from Table 1 that the aliphatic alcohols having an odd number of carbon atoms and the esters thereof have significant hair-growing effects whereas the aliphatic alcohols having even-numbered carbon chains as long as the former and the esters thereof have no hair-growing effect.

Test 2: Human Study for Evaluating Effectiveness

Aliphatic alcohols having an odd number of carbon atoms and derivatives thereof were tested for their skin vivifying effects.

The tested substances and their formulations were the same as in Test 1.

Forearms of healthy people were washed with soap to remove skin oil. After one hour of the washing, each forearm was measured for its electroconductivity of the skin (Casual value) and blood flow (using laser-Doppler blood flow meter). Since the electroconductivity of the skin is proportional to the amount of water retained in the skin, it can be used as an indicator of skin moisture-retaining capability of the sample.

Thereafter, each sample was applied on the skin of a forearm four times a day for 2 weeks. Two hours after the last application, the sample-applied portion of the forearm was washed with soap. One hour after the washing, the electroconductivity and the blood flow were determined. The results are shown in Table 2. In table 2, electroconductivity of the skin and the blood flow determined after application of sample are expressed as an index taking the value obtained before the application of sample as 100.

TABLE 2

| Test Substance | Concentration (% by weight) | EC*1 | OE*2 | SBF*3 | OE |
|---|---|---|---|---|---|
| Amyl Alcohol | 1.0 | 125 | EF*4 | 143 | EF |
| Heptyl Alcohol | 1.0 | 128 | EF | 145 | EF |
| Nonyl Alcohol | 1.0 | 128 | EF | 145 | EF |
| Undecyl Alcohol | 1.0 | 127 | EF | 142 | EF |
| Tridecyl Alcohol | 1.0 | 129 | EF | 143 | EF |
| Pentadecyl Alcohol | 1.0 | 130 | EF | 148 | EF |
| Heptadecyl Alcohol | 1.0 | 163 | EF | 167 | EF |
| Nonadecyl Alcohol | 1.0 | 150 | EF | 155 | EF |
| Uneicosyl Alcohol | 1.0 | 145 | EF | 130 | EF |
| Trieicosyl Alcohol | 1.0 | 140 | EF | 135 | EF |
| Pentaeicosyl Alcohol | 1.0 | 125 | EF | 115 | EF |
| Butyl Alcohol | 1.0 | 101 | IE*5 | 97 | IE |
| Hexyl Alcohol | 1.0 | 100 | IE | 99 | IE |
| Octyl Alcohol | 1.0 | 98 | IE | 99 | IE |
| Decyl Alcohol | 1.0 | 105 | IE | 100 | IE |
| Lauryl Alcohol | 1.0 | 103 | IE | 104 | IE |
| Myristyl Alcohol | 1.0 | 102 | IE | 101 | IE |
| Cetyl Alcohol | 1.0 | 100 | IE | 97 | IE |
| Stearyl Alcohol | 1.0 | 103 | IE | 99 | IE |
| Eicosyl Alcohol | 1.0 | 97 | IE | 99 | IE |
| Behenyl Alcohol | 1.0 | 96 | IE | 98 | IE |
| Lignoceryl Alcohol | 1.0 | 99 | IE | 100 | IE |
| Nonyl Succinate | 0.3 | 125 | EF | 123 | EF |
| Undecanyl Succinate | 0.3 | 135 | EF | 145 | EF |
| Nonyl Citrate | 0.3 | 115 | EF | 128 | EF |
| Undecanyl Citrate | 0.3 | 121 | EF | 128 | EF |
| Nonyl Fumarate | 0.3 | 127 | EF | 135 | EF |
| Undecanyl Fumarate | 0.3 | 128 | EF | 126 | EF |
| Undecyl Decanoate | 5.0 | 129 | EF | 127 | EF |
| Undecyl Linoleate | 5.0 | 131 | EF | 130 | EF |
| Lauryl Decanoate | 5.0 | 105 | IE | 100 | IE |
| Lauryl Linoleate | 5.0 | 121 | EF | 118 | EF |
| Tridecyl Decanoate | 5.0 | 128 | EF | 125 | EF |
| Tridecyl Linoleate | 5.0 | 130 | EF | 123 | EF |

*1 Electroconductivity (indicating skin moisture-Retaining capability)
*2 Overall Evaluation
*3 Skin Blood Flow
*4 Effective
*5 Ineffective It can be seen from Table 2 that the aliphatic alcohols having an odd number of carbon atoms and the esters thereof have significant skin-vivifying effects whereas the aliphatic alcohols having even-numbered carbon chains as long as the former and the esters thereof have no skin-vivifying effect.

Test 3: Animal Study for Evaluating Effectiveness

The compositions containing as effective ingredients an aliphatic alcohol having odd number of carbon atoms and aliphatic carboxylic acid having odd number of carbon atoms were tested for their hair-growing effect.

The test samples were mixtures of an aliphatic alcohol having odd or even number of carbon atoms or its ester and aliphatic carboxylic acid having odd or even number of carbon atoms or its triglyceride, and as controls, carboxylic acids having odd number of carbon atoms and triglycerides thereof. Further, ethanol containig no test substance was also tested as a control. Every test substance was dissolved in ethanol to a concentration of 0.3 to 5.0% by weight. The ratios of alcohol or its ester to carboxylic acid or its triglyceride in a mixture was 1:9 to 9:1.

From the backs of Hartley guinea pigs, hair was removed. Each test sample was applied on a back from which hair had been removed 3 times a week for 4 weeks. Length of hair growed on the back was measured every week. The results are shown in table 3. In table 3, the increase in the length of hair in a week is also shown. Each value shown in table 3 is the average of 20 hairs and expressed in millimeters. In table 3, "H.L." means hair length, and "IHL" means increase in hair length in a week.

From table 3, it can be seen that the mixtures of aliphatic alcohol of odd numbered carbon atoms or its ester and aliphatic carboxylic acid of odd numbered carbon atoms have stronger hair-growing effect than ethanol and those mixtures of aliphatic alcohol of even-numbered carbon atoms or its ester and aliphatic carboxylic acid of even-numbered carbon atoms and its triglyceride. Further, the former has stronger hair-growing effect when compared with aliphatic carboxylic acids or their triglycerides alone.

of n-trihendecanoin, 1.0 wt % of castor oil, 0.5 wt % of pyrrolidone carboxylic acid, 0.5 wt % of perfume and 86.0% of ethanol was prepared. This composition was then used by patients (totalling 14 patients) suffering from Alopecia praematura and praesenilis, and Alopecia areata over a period of 4 to 6 months. About 2 ml of the composition was applied on the scalp every day. The hair-growing effect of the composition was evaluated by photographs taken before and after the treatment, observation by third person, and subjective observation by the patients themselves. The results are shown in table 4. Further, no side effects were observed for all patients.

TABLE 4

| Alopecia | Number of Cases | Results | | |
|---|---|---|---|---|
| | | Remarkably Effective | Effective | Ineffective |
| Alopecia praematura and praesenilis | 10 | 5 | 4 | 1 |
| Alopecia Areata | 4 | 2 | 2 | 0 |

Test 5: Human Study for Evaluating Safety

Pieces of gauze of 1 cm in diameter were soaked with the hair-growing composition prepared for Test 4. As a control, pieces of gauze of 1 cm in diameter were soaked with water.

Two pieces of each type of gauze (totalling 4 pieces) were attached as a closed patch by means of a fin chamber to the antebrachial flexor side of 25 healthy females for 24 hours. The skin conditions were observed after 30 minutes and 24 hours of the removal of the gauze. The result was that none of the women had any skin irritation.

The following indicates forms and compositions as examples of the cell-stimulating composition of the present invention. In the following, the compositions are expressed in terms of % by weight.

TABLE 3

| Test Substance (conc.) | 1st Week H.L. | 2nd Week H.L. | IHL. | 3rd Week H.L. | IHL. | 4th Week H.L. | IHL. |
|---|---|---|---|---|---|---|---|
| Ethanol | 5.9 ± 0.2 | 10.9 ± 0.5 | 5.0 | 16.0 ± 0.7 | 5.1 | 19.9 ± 0.8 | 3.9 |
| Myristic Acid (0.3 wt %) Stearyl Alcohol (2.0 wt %) | 5.8 | 10.8 ± 0.5 | 5.0 | 16.0 ± 0.6 | 5.2 | 19.8 ± 0.8 | 3.8 |
| Trimyristin (5.0 wt %) Lauryl Stearate (1.0 wt %) | 5.9 | 10.9 ± 0.6 | 5.0 | 16.1 ± 0.6 | 5.2 | 20.7 ± 0.7 | 3.9 |
| Lauric Acid (0.3 wt %) Palmitic Alcohol (2.0 wt %) | 6.0 | 11.0 ± 0.5 | 5.0 | 16.1 ± 0.7 | 5.1 | 20.1 ± 0.7 | 4.0 |
| Tripalmitin (5.0 wt %) Lauryl Palmitate (1.0 wt%) | 5.9 | 11.0 ± 0.4 | 5.1 | 16.0 ± 0.6 | 5.0 | 19.8 ± 0.8 | 3.8 |
| Pentadecanoic Acid (0.3 wt %) | 6.1 | 11.2 ± 0.4 | 5.1 | 17.0 ± 0.6 | 6.8 | 21.0 ± 0.8 | 4.0 |
| Tritridecanoin (5.0 wt %) | 6.3 | 11.0 | 4.7 | 16.5 ± 0.5 | 5.5 | 20.5 ± 0.7 | 4.0 |
| Triheptadecanoin (5.0 wt %) | 6.2 | 11.2 ± 0.5 | 5.0 | 17.2 ± 0.5 | 6.0 | 21.1 ± 0.7 | 4.0 |
| Pentadecanoic Acid (0.3 wt %) Pentadecanol (2.0 wt %) | 7.0 | 14.2 ± 0.5 | 7.2 | 21.0 ± 0.6 | 6.8 | 25.0 ± 0.8 | 4.0 |
| Tripentadecanoin (5.0 wt %) Undecanol (1.0 wt %) | 7.5 | 15.0 ± 0.5 | 7.5 | 22.0 ± 0.6 | 7.0 | 25.2 ± 0.8 | 3.2 |
| Tritridecanoin (5.0 wt %) Undecyl Palmitate (1.0 wt %) | 7.8 | 15.3 ± 0.5 | 7.5 | 22.6 ± 0.6 | 7.3 | 25.5 ± 0.8 | 2.9 |
| Triheptadecanoin (5.0 wt %) Undecanol (1.0 wt %) | 7.6 | 15.0 ± 0.5 | 7.4 | 22.3 ± 0.6 | 7.3 | 25.5 ± 0.8 | 2.9 |
| Tripentadecanoin (5.0 wt %) Undecyl Palmitate (1.0 wt %) | 7.5 | 15.3 ± 0.5 | 7.8 | 22.8 ± 0.6 | 7.5 | 25.5 ± 0.8 | 2.7 |

Test 4: Human Study for Evaluating Effectiveness

The cell-stimulating composition of the present invention consisting of 2.0 wt % of undecanol, 10.0 wt %

| Ingredient | Content |
|---|---|
| Example 1 Hair-Growing Agent | |

| Ingredient | Content |
|---|---|
| 80% Ethanol | 88 |
| Tri-n-undecylglyceryl Ether | 10.0 |
| Castor Oil | 1.0 |
| Pyrrolidone Carboxylic Acid | 0.5 |
| Perfume | 0.5 |
| Example 2 | |
| Hair-Growing Agent | |
| 85% Ethanol | 97.5 |
| n-Nonyl Alcohol | 0.5 |
| Olive Oil | 1.0 |
| α-Tocopherol | 0.5 |
| Perfume | 0.5 |
| Example 3 | |
| Hair-Growing Agent | |
| 90% Ethanol | 92.5 |
| Tri-n-tridecylglyceryl Ether | 5.0 |
| Olive Oil | 1.0 |
| Perfume | 0.5 |
| Example 4 | |
| Hair-Growing Agent | |
| 90% Ethanol | 89.5 |
| n-Tridecyl Acetate | 3.0 |
| Liquid Paraffin | 5.0 |
| Polyethylene Glycol | 2.0 |
| Perfume | 0.5 |
| Example 5 | |
| Hair Shampoo Composition | |
| Lauryl Ether Sodium Sulfate | 5.0 |
| α-olefin sodium sulfonate | 10.0 |
| Lauryl Sulfate Triethanol Amine | 5.0 |
| Tri-n-tridecylglyceryl Ether | 3.0 |
| Purified Water | 77.0 |
| Example 6 | |
| Hair Rinse Composition | |
| Stearyltrimethyl Ammonium Chloride | 1.5 |
| Distearyldimethyl Ammonium Chloride | 0.5 |
| Cetyl Alcohol | 1.5 |
| Polyoxyethylene Stearyl Ether ($\overline{P} = 5$) | 2.0 |
| Liquid Paraffin | 1.0 |
| Triundecylglyceryl Ether | 3.0 |
| Purified Water | 90.5 |
| Example 7 | |
| Hair Cream Composition | |
| Tri-n-pentadecylglyceryl Ether | 10.0 |
| Olive Oil | 5.0 |
| Liquid Paraffin | 51.0 |
| Beeswax | 1.0 |
| Sorbitan Sesquioleate | 3.0 |
| Purified Water | 30.0 |
| Example 8 | |
| Hair Tonic Composition | |
| Nonyl Acetate | 3.0 |
| Chillies Tincture | 0.5 |
| Hinokitiol | 0.1 |
| α-tocopherol | 0.3 |
| Castor Oil | 10.0 |
| Ethanol | 86.1 |
| Example 9 | |
| Hydrophilic Ointment | |
| White Vaseline | 25 |
| Stearyl Alcohol | 22 |
| Propyleneglycol | 12 |
| Sodium Lauryl Sulfate | 12 |
| Paraoxy Ethylbenzoate | 0.025 |
| Paraoxy Propylbenzoate | 0.015 |
| n-trihendecanol | 10.0 |
| Perfume | 0.5 |
| Purified Water | Balance |
| Example 10 | |
| Liquid Cream (o/w emulsion type) | |
| Stearic Acid | 1.5 |
| Cetyl Alcohol | 1.5 |
| Vaseline | 4.0 |
| Liquid Paraffin | 8.0 |
| Polyoxyethylene (10 mole) Monoleate | 2.0 |
| Triethanol Amine | 1.0 |
| n-heptadecanol | 4.0 |
| Perfume | 0.5 |
| Purified Water | Balance |
| Example 11 | |
| Shaving Cream | |
| Stearic Acid | 22.0 |
| Coconut Oil | 10.0 |
| Palm Oil | 5.0 |
| Potassium Hydroxide | 7.0 |
| Sodium Hydroxide | 1.5 |
| Glycerin | 10.0 |
| n-pentadecanol | 8.0 |
| Perfume | 0.5 |
| Purified Water | Balance |
| Example 12 | |
| Deodorant Stick | |
| Zinc Oxide | 12.0 |
| Paraffin Wax | 12.0 |
| Beeswax | 20.0 |
| Vaseline | 20.0 |
| Liquid Paraffin | 25.5 |
| Aluminum Hydrochloride | 5.0 |
| Triheptadenol | 5.0 |
| Perfume | 0.5 |
| Example 13 | |
| After-Shaving Lotion | |
| Glycerin | 4.0 |
| Boric Acid | 1.0 |
| Ethanol | 18.0 |
| Menthol | 0.1 |
| Undecyl Stearate | 3.0 |
| Perfume | 0.3 |
| Purified Water | Balance |
| Example 14 | |
| Hair-Growing Agent | |
| n-trihendecanoin | 10.0 |
| Undecanol | 2.0 |
| Castor Oil | 1.0 |
| Pyrrolidone Carboxylic Acid | 0.5 |
| Perfume | 0.5 |
| Ethanol | 86 |
| Example 15 | |
| Hair-Growing Agent | 3.0 |
| Ethyl n-tridecanoate | 1.0 |
| Liquid Paraffin | 5.0 |
| Polyethyleneglycol | 2.0 |
| Ethanol | 88 |
| Perfume | 1.0 |
| Example 16 | |
| Hair-Growing Agent | |
| Tripentadecanoin | 4.0 |
| Undecanol | 1.0 |
| Olive Oil | 1.0 |
| Glycyrrhizin | 1.0 |
| Perfume | 0.5 |
| Ethanol | 92.5 |
| Example 17 | |
| Hair Tonic | |
| Tripentadecanoin | 3.0 |
| Undecyl Stearate | 0.5 |
| α-tocopherol | 0.3 |
| Hinokitiol | 0.1 |
| Castor Oil | 10.0 |
| Ethanol | 77.5 |
| Perfume | 0.5 |
| Example 18 | |
| Hair Shampoo | |
| Lauryl Ether Sodium Sulfate | 5.0 |
| α-olefin Sodium Sulfonate | 10.0 |
| Lauryl Sulfate Triethanol Amine | 5.0 |
| n-tritridecanoin | 2.5 |
| Pentadecyl Alcohol | 0.5 |
| Purified Water | 76.5 |
| Perfume | 0.5 |
| Example 19 | |
| Hair Rinse | |
| Stearyltrimethyl Ammonium Chloride | 1.5 |
| Distearyldimethyl Ammonium Chloride | 0.5 |
| Cetanol | 1.5 |
| Polyoxyethylene Stearyl Ether ($\overline{P} = 5$) | 1.5 |

| Ingredient | Content |
| --- | --- |
| Liquid Paraffin | 1.0 |
| Pentadecanol | 0.5 |
| Tripentadecanoin | 3.0 |
| Purified Water | 90.0 |
| Perfume | 0.5 |

What is claimed is:

1. A method of stimulating growth of human hair on a human head suffering from or susceptible to alopecia, which comprises bringing active human hair follicles on a human head from a telogen state into a normal anagen state by applying to said follicles a growth stimulating amount of an effective ingredient which is an aliphatic alcohol selected from the group consisting of n-heptyl alcohol, n-nonyl alcohol, n-undecyl alcohol, n-tridecyl alcohol, n-pentadecyl alcohol, n-heptadecyl alcohol, n-nonadecyl alcohol, n-uneicosyl alcohol, n-tricosyl alcohol and n-pentacosyl alcohol.

* * * * *